(12) United States Patent
Toya et al.

(10) Patent No.: US 6,271,418 B1
(45) Date of Patent: Aug. 7, 2001

(54) PROCESS FOR PREPARING (HETERO) AROMATIC SUBSTITUTED BENZENE DERIVATIVES

(75) Inventors: Tetsuya Toya, Saitama-ken; Hidetoshi Shirakura; Junichi Kon, both of Ibaraki-ken, all of (JP)

(73) Assignee: Nippon Kayaku Co., Ltd., Tokyo (JP)

( * ) Notice: Subject to any disclaimer, the term of this patent is extended or adjusted under 35 U.S.C. 154(b) by 0 days.

(21) Appl. No.: 09/512,151

(22) Filed: Feb. 22, 2000

(51) Int. Cl.$^7$ .................. C07C 211/00; C07C 209/00
(52) U.S. Cl. .................. 564/1; 564/305; 564/412; 564/446; 564/449
(58) Field of Search .................. 564/1, 305, 412, 564/446, 449

(56) References Cited

U.S. PATENT DOCUMENTS

| | | | |
|---|---|---|---|
| 4,247,479 | * | 1/1981 | Berthold ........................ 564/436 |
| 4,900,754 | | 2/1990 | Regan et al. ................... 514/459 |

FOREIGN PATENT DOCUMENTS

| | | |
|---|---|---|
| 0 061 128 | 9/1982 | (EP) . |
| 2 041 915 | 9/1990 | (GB) . |
| 56-125340 | 1/1981 | (JP) . |
| 7-252183 | 10/1995 | (JP) . |
| 11-49721 | 2/1999 | (JP) . |
| 11-49722 | 2/1999 | (JP) . |
| 91/13065 | 9/1991 | (WO) . |
| 91/13616 | 9/1991 | (WO) . |
| 94/01440 | 1/1994 | (WO) . |
| 98/20011 | 5/1998 | (WO) . |
| 98/50030 | 11/1998 | (WO) . |
| 99/20611 | 4/1999 | (WO) . |
| 99/20612 | 4/1999 | (WO) . |
| 99/41231 | 8/1999 | (WO) . |
| 99/41235 | 8/1999 | (WO) . |
| 00/02859 | 1/2000 | (WO) . |

OTHER PUBLICATIONS

Lin, S.T.;Yang,F.; Liang, D.; Shiao.M.; Electron impact mass spectra of some arylphyridines; J. Chin. Chem. Soc. (Taipei), vol. 44, No. 5, 1997, pp. 527–533.

Shiao, M.J.; Perng, C.Y.; Shen, C.C.; J. Chin. Chem.Soc. (Taipei), 1991, vol. 38, No. 1, pp. 47–50.

Chemical Abstracts, Abstract No. 78:71879 1972.

Chemical Abstracts, Abstract No. 61:16051 1964.

Bezborodov, V.S. et al., "Reduction of 6–acetyl–3–aryl–2–cyclohexanones by sodium borohydride", Zh.Org.Khim, 1992, vol. 28, No. 7, pp. 1544–1545.

Yamamoto, Yoshihiko et al., "Synthesis of Phenolic Biaryls and p–Terphenyls and Their Heteroaromatic Analogs via a Cycloaddition Route Using 4–Aryl–2–silyloxybuta–1, 3–dienes and Electron–Deficient Alkynes", Synthesis, 1996, No. 8, pp. 949–953.

Ram V. J.; Goel A.; Ring transformation Reactions Part IV: 6–Aryl–3–methoxy–carbonyl–4–methylthio–2H–pyran –2–one, A Novel Synthon for the Synthesis of 1,3–Terphenyls from Aryl Ketones; Tetrahedron Lett., vol. 37, No. 1, 1996, pp. 93–96.

Fujita, M.; Oka,H.; Ogura, K.; Palladium(0)/LiCl Promoted Cross–Coupling Reaction of (4–Pyridyl) stannanes and Aromatic Bromides: Easy Access to Poly(4–Pyridyl)–Substituted Aromatics Tetrahedron Lett., vol. 36, No. 29, 1995, pp. 5247–5250.

Kelly T. Ross et al. "A Chiral Catechol with C2 Symmetry", J.Org. Chem., 1989, vol. 54, No. 4, pp. 980–983.

Katritzky, Alan R. et al. "Improved Syntheses of 3,5–Diaryl–Substituted Phenols", J.Org.Chem., 1997, vol. 62, No. 23, pp. 8215–8217.

Harrison, Ernest A., Jr., "Benzodioxole Chemistry.3. 1aPreparation and Selected Reactions of 3a,4,7,7a–Tetrahydro–4,7–methano–1,3–benzodioxole–2, 8–diones. 1b Novel Hydroxide Ion Induced Aromatization of Carbonyl–Bridged Cyclic Carbonates1c", J. Org. Chem., 1979, vol. 44, No. 11, pp. 1807–1811.

Sambaiah, Thota et al., "Highly Regio–and Stereoselective Cocyclotrimerization and Linear Cotrimerization of α, β–Unsaturated Carbonyl Compounds with Alkynes Catalyzed by Nickel Complexes", J. Org.Chem., 1999, vol. 64, No. 10, pp. 3663–3670.

Shen, Wang et al., "Potent Inhibitors of Protein Farnesyltransferase:Heteroarenes as Cysteine Replacements", Bioorg. Med. Chem. Lett., 1999, vol. 9, No. 5, pp. 703–708.

Augeri, David J. et al., "Potent and orally bioavailable noncysteine–containing inhibitors of protein farnesyltransferase", Bioorg. Med. Chem. Lett., 1999, vol. 9, No. 8, pp. 1069–1074.

J.Med. Chem. 1981, 24, 1006–1010; Yasumitsu Tamura; "Nonsteroidal Antiinflammatory Agents. 341 Synthesis of the Positional Isomers of 4'–Chloro–5–methoxy–3–biphenylylacetic Acid and Their Antiinflammatory and Analgesic Activities".

Heterocycles, 1986, vol. 24 No. 7, pp. 1963–1971; Matsumoto, et al.; "Synthesis of 4–Cyanoindole From 4–Oxo–4, 5,6,7,–Tetrahydroindole Derivatives".

(List continued on next page.)

*Primary Examiner*—Jezia Riley
(74) *Attorney, Agent, or Firm*—Nields & Lemack

(57) ABSTRACT

Three processes are described for preparing (hetero) aromatic substituted benzene derivatives which comprise aromatization of cyclohexenone derivatives via (chloro) cyclohexadiene derivatives.

12 Claims, No Drawings

OTHER PUBLICATIONS

Tetrahedron, 1999, 55, 8579–8586; Beccalli, et al.; "6–Chloro–spirocyclohexenindol–2–ones: an Unusual ring Transformation to Ethyl 2–(Cyclohexa–1,4–dienyl)phenyl-carbamates".

Chemistry and Industry, Nov. 15, 1980, 888–889; Tamura, et al.; "An improved method for the conversion of cyclohexenones into anisoles".

Tetrahedron Letters, vol. 36, No. 46, pp. 8395–8398, 1995; Hegde, et al.; "Aromatization of Cyclohexenones with Iodine/Sodium Alkoxide. A Regioselective synthesis of 2–Iodophenols".

Tetrahedron Letters 40 (1999) 45–48; McBride, et al.; "Efficient Synthesis of Substituted Benzenes From 1,3–Dienes of 1,4–Cyclohexadienes With KMnO4 Under Mild Conditions".

Tetrahedron Letters, vol. 31, No. 4, pp. 481–484, 1990; Atul S. Kotnis; "A Repaid Entry to Highly Functionalized p–Methoxybenzoates: Synthesis of Aromatic Portion of Milbemycin β3†".

* cited by examiner

PROCESS FOR PREPARING (HETERO) AROMATIC SUBSTITUTED BENZENE DERIVATIVES

FIELD OF THE INVENTION

This invention pertains to the field of pharmaceutical chemistry and provides advantageous processes for substituted benzene derivatives. More specifically, the process relate to the preparation of (hetero)aromatic substituted benzene derivatives by aromatizing cyclohexenone derivatives.

BACKGROUND OF THE INVENTION

Conventionally, biphenyl derivatives have been prepared by a coupling reaction under various reacting condition.

Ann. (1904), 332, 38 and JP4-257564 discloses Ullman coupling reaction of halobenzene derivatives in the presence of metal, Na or Cu etc.

Bull. Chem. Soc. Jpn. (1976), 49, 1958 teaches a nickel-phosphine complex catalyzed coupling of aryl Grignard reagent with haloaryl derivative.

JP6-9536 discloses a cross coupling reaction of 2-chlorobenzonitrile and aryl Grignard reagent in the presence of $MnCl_2$.

Synth. Commun. (1981), 11, 513 teaches palladium catalyzed coupling reaction of aryl iodide, aryl bromide or aryl trifulate with aryl boronic acid derivative.

A major disadvantage of coupling processes in the art is 1) use of expensive starting material and catalyst, 2) low selectivity of the reaction resulted in a mixture of homo and cross coupling products, 3) difficulty in isolation and purification processes, 4) handling of highly reactive reagents, Grignard reagent etc.

Construction of benzene ring is another method to prepare biphenyl derivatives. JP9-87238 discloses a cycloaddition reaction of α-cyanocinnamate derivative with butadiene to afford benzene substituted cyclohexene derivative followed by aromatization. This method needs high pressure and temperature in the cycloaddition process.

The present invention provides an industrial process by which biphenyl derivatives can be prepared in a high selectivity and yield and which is free from the above-mentioned disadvantages.

SUMMARY OF THE INVENTION

The present invention provides three processes for preparing substituted benzene derivatives represented by the formula (I):

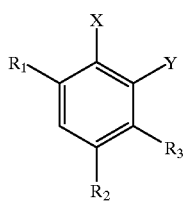

(I)

wherein X represents a phenyl group, a naphthyl group or a heteroaromatic group which are optionally substituted with $(C_1-C_4)$alkyl group(s), $(C_1-C_4)$alkoxy group(s), halogen atom(s) or nitro group(s); Y represents a $(C_1-C_4)$ alkoxycarbonyl group, a cyano group, a nitro group or a $(C_1-C_4)$alkoxysulfonyl group; $R_1$, $R_2$ and $R_3$ each independently represent a hydrogen atom, a $(C_1-C_4)$alkyl group, a $(C_1-C_4)$alkoxy group or a phenyl group which is optionally substituted with $(C_1-C_4)$alkyl group(s), $(C_1-C_4)$alkoxy group(s) or halogen atom(s); which comprise aromatizing cyclohexenone derivatives represented by the formula (II):

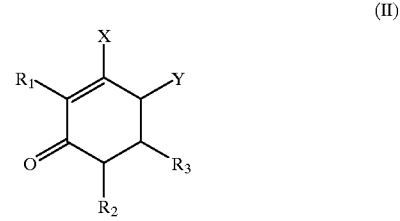

(II)

wherein X, Y, $R_1$, $R_2$ and $R_3$ have the same meanings as defined above.

The first process comprises chlorinating a cyclohexenone derivative represented by the formula (II):

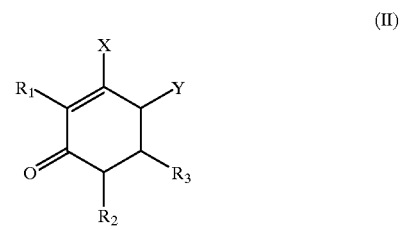

(II)

wherein X, Y, $R_1$, $R_2$ and $R_3$ have the same meanings as defined above, to obtain a halocyclohexadiene derivative or a mixture of isomers represented by the formula (IIIA and/or IIIB):

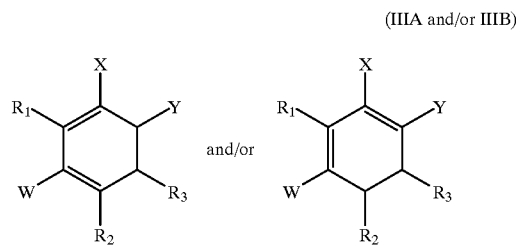

(IIIA and/or IIIB)

wherein X, Y, $R_1$, $R_2$ and $R_3$ are as defined above and W represents a halogen atom, followed by dehydro-, dehalogenation to a benzene derivative represented by the formula (1):

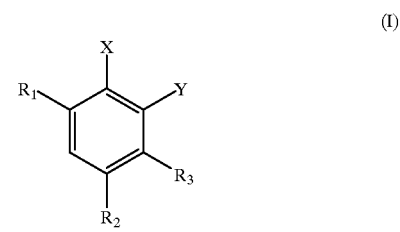

(I)

wherein X, Y, $R_1$, $R_2$ and $R_3$ have the same meanings as defined above.

The second process comprises halogenating a cyclohexenone derivative represented by the formula (II):

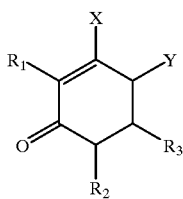
(II)

wherein X, Y, R$_1$, R$_2$ and R$_3$ have the same meanings as defined above, to obtain a halocyclohexadiene derivative or a mixture of isomers represented by the formula (IIIA and/or IIIB):

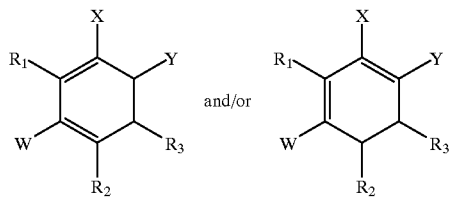
(IIIA and/or IIIB)

wherein X, Y, W, R$_1$, R$_2$ and R$_3$ have the same meanings as defined above, followed by dehydrogenation and reduction to a benzene derivative represented by the formula (I):

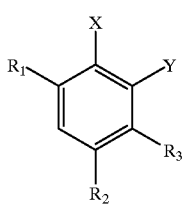
(I)

wherein X, Y, R$_1$, R$_2$ and R$_3$ have the same meanings as defined above.

The third process comprises reducing a cyclohexenone derivative represented by the formula (II):

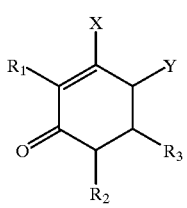
(II)

wherein X, Y, R$_1$, R$_2$ and R$_3$ have the same meanings as defined above, to obtain a cyclohexenol derivative represented by the formula (V):

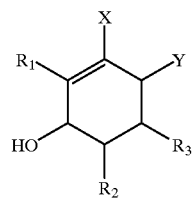
(V)

wherein X, Y, R$_1$, R$_2$ and R$_3$ have the same meanings as defined above, followed by dehydration and dehydrogenation to a benzene derivative represented by the formula (I):

(I)

wherein X, Y, R$_1$, R$_2$ and R$_3$ have the same meanings as defined above.

DETAILED DESCRIPTION OF THE INVENTION

The present invention will now be described in detail below.

In this document, all temperatures are stated in degrees Celsius. All amounts, ratios, concentrations, proportions and the like are stated in weight units unless otherwise stated, except for ratios of solvents which are in volume units.

The first process is summarized in the scheme 1 as showed below.

Scheme 1

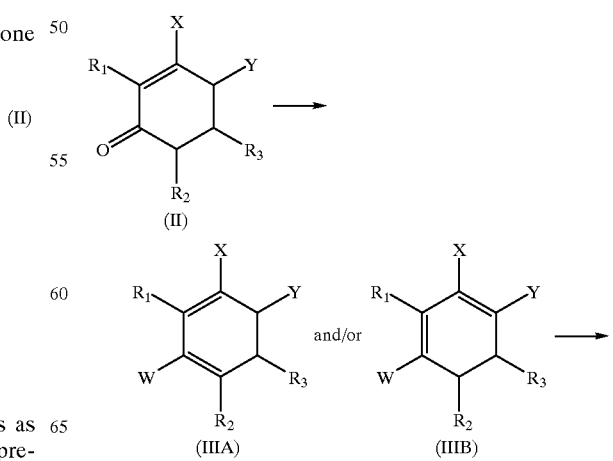

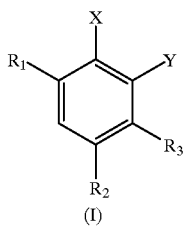

(I)

A cyclohexenone derivative represented by the formula (II):

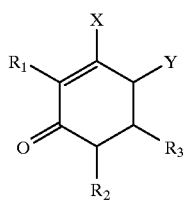

(II)

wherein X, Y, R$_1$, R$_2$ and R$_3$ have the same meanings as defined above, is reacted with a halogenating agent in a solvent to obtain a halocyclohexadiene derivative or a mixture of isomers represented by the formula (IIIA and/or IIIB):

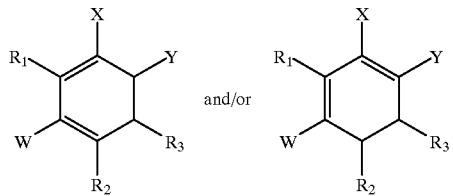

(IIIA and/or IIIB)

wherein X, Y, W, R$_1$, R$_2$ and R$_3$ have the same meanings as defined above.

Any ratio of the isomers (IIIA and IIIB) may be employed.

As the halogenating agent, there may be used chlorinating agent such as thionyl chloride, oxalyl chloride, phosgen, phosphorus oxychloride, phosphorus pentachloride, etc. and brominating agent such as thionyl bromide, phosphorus oxybromide, etc. The agent may be used in a stoichiometrical amount or 0.5 to 10 times the stoichiometrical amount, but preferably a stoichiometrical amount or 0.8 to 5 times the stoichiometrical amount.

As the solvent, any solvent inert to a reactant and a reagent may be used. There may be mentioned aliphatic hydrocarbons such as n-hexane, n-heptane, etc., aromatic hydrocarbons such as toluene, xylene, etc., halogenated hydrocarbons such as dichloromethane, chlorobenzene, etc., aliphatic esters such as ethyl acetate, butyl acetate, etc., and ethers such as tetrahydrofuran, etc., but preferably aliphatic hydrocarbons, aromatic hydrocarbons and halogenated hydrocarbons. A mixed solvent of the above may be used. And this step also may be carried out without a solvent.

The reaction can be carried out at a temperature from −20° C. to the boiling point of the solvent, but preferably in the range from 0° C. to the boiling point of the solvent.

If necessary, a catalyst such as N,N-dimethylformamide may be added to the reaction system. The catalyst may be used in a stoichiometrical amount or 0.01 to 5 times the stoichiometrical amount, but preferably a stoichiometrical amount or 0.05 to 3 times the stoichiometrical amount.

A halocyclohexadiene derivative or a mixture of isomers represented by the formula (IIIA and/or IIIB):

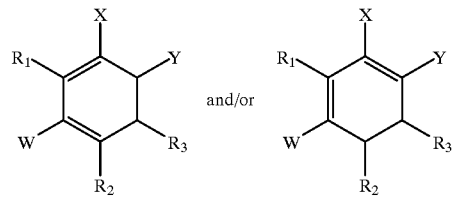

(IIIA and/or IIIB)

wherein X, Y, W, R$_1$, R$_2$ and R$_3$ have the same meanings as defined above, is reacted with a dehydro-, dehalogenating agent in a solvent to obtain a benzene derivative represented by the formula (I):

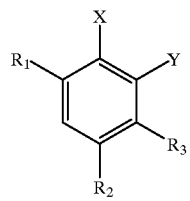

(I)

wherein X, Y, R$_1$, R$_2$ and R$_3$ have the same meanings as defined above.

As the dehydro-, dehalogenating agent, a base may be used. There may be used alkaline metal hydroxides such as potassium hydroxide, sodium hydroxide, etc., alkaline metal carbonates such as potassium carbonate, sodium carbonate, etc., alkaline metal alkoxides such as sodium methoxide, sodium ethoxide, potassium t-butoxide, etc., alkaline metal hydrides such as sodium hydride etc. and organic bases such as pyridine, triethylamine, etc., but preferably alkaline metal hydroxides. The base may be used in a stoichiometrical amount or 0.5 to 20 times the stoichiometrical amount, but preferably a stoichiometrical amount or 0.8 to 10 times the stoichiometrical amount.

As the solvent, any solvent inert to a reactant and a reagent may be used. There may be mentioned aliphatic alcohols such as methanol, ethanol, etc., aromatic hydrocarbons such as toluene, xylene, etc., halogenated hydrocarbons such as dichloromethane, chlorobenzene, etc., ethers such as tetrahydrofuran, etc., amides such as N,N-dimethylformamide etc., sulfoxides such as dimethylsulfoxide, etc. and water, but preferably aliphatic alcohol, aromatic hydrocarbons, ethers and water. A mixture of the solvents which are described above may be used.

The reaction can be carried out at a temperature from −20° C. to the boiling point of the solvent, but preferably in the range from 0° C. to the boiling point of the solvent.

The second process is summarized in the scheme 2 as shown below.

Scheme 2

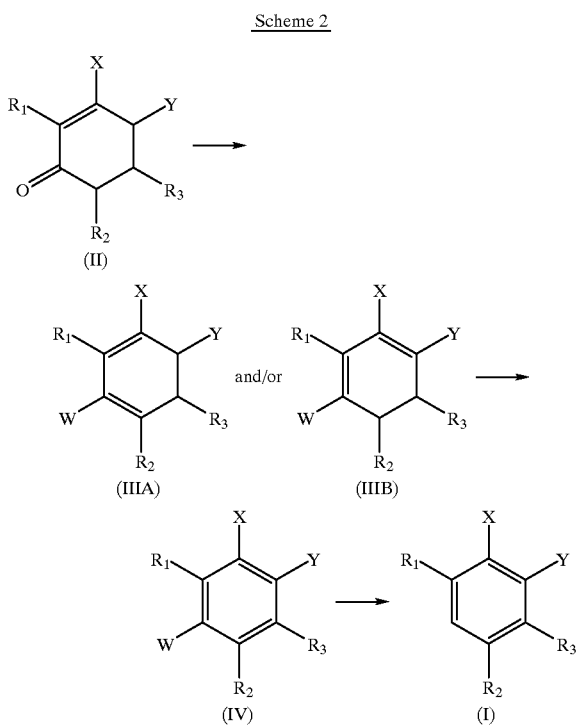

The first step of this process is the same one as described above.

A halocyclohexadiene derivative or a mixture of isomers represented by the formula (IIIA and/or IIIB):

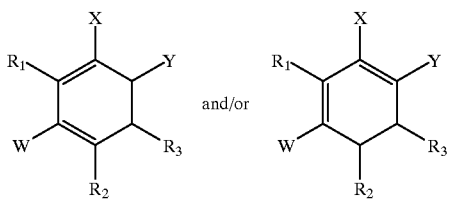
(IIIA and/or IIIB)

wherein X, Y, W, $R_1$, $R_2$ and $R_3$ have the same meanings as defined above, is reacted with a dehydrogenating agent in a solvent to obtain a halobenzene derivative represented by the formula (IV):

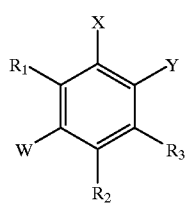
(IV)

wherein X, Y, W, $R_1$, $R_2$ and $R_3$ have the same meanings as defined above.

As the dehydrogenating agent, an oxidizing agent or a base may be used. There may be mentioned oxidizing agent such as metal oxides(potassium permanganate, etc.), platinum group metal(platinum, palladium, osmium, iridium, ruthenium, rhodium, etc.) or it's salt with mineral acid such as hydrochloride, halogenating agents(thionyl chloride, sulfulyl chloride, etc.), quinones(DDQ, etc.) and sulfur. These agents may be used under oxygen. The platinum group metal and their salt with hydrochloride may be supported on a carrier such as activated charcoal, graphite, silica, alumina, silica-alumina, zeolite, zirconia, diatomaceous earth, barium sulfate, etc. The oxidizing agent may be used in a stoichiometrical amount or 0.001 to 20 times the stoichiometrical amount, but preferably a stoichiometrical amount or 0.05 to 10 times the stoichiometrical amount. These agents may be used under oxygen.

As the base, there may be used alkaline metal hydroxides such as potassium hydroxide, sodium hydroxide, etc., alkaline metal carbonates such as potassium carbonate, sodium carbonate, etc., alkaline metal alkoxides such as sodium methoxide, sodium ethoxide, potassium t-butoxide, etc., alkaline metal hydrides such as sodium hydride etc., but preferably alkaline metal alkoxides. The base may be used in a stoichiometrical amount or 0.5 to 20 times the stoichiometrical amount, but preferably a stoichiometrical amount or 0.8 to 10 times the stoichiometrical amount.

As the solvent, any solvent inert to a reactant and a reagent may be used. There may be mentioned aliphatic alcohols such as methanol, ethanol, etc., aromatic hydrocarbons such as toluene, xylene, etc., aliphatic hydrocarbons such as n-hexane, n-heptane, etc., halogenated hydrocarbons such as dichloromethane, 1,2-dichloroethane, chlorobenzene, etc., esters such as ethyl acetate, butyl acetate, methyl benzoate, etc., ethers such as tetrahydrofuran, etc., nitrites such as acetonitrile etc., organic acids such as acetic acid, etc., and water, but preferably aliphatic hydrocarbons, aromatic hydrocarbons, halogenated hydrocarbons, ethers, nitriles, organic acids and water. A mixed solvent of the above also may be used.

The reaction can be carried out at a temperature from 20 to 400° C., but preferably in the range from 50° C. to 300° C.

A halobenzene derivative represented by the formula (IV):

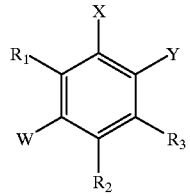

wherein X, Y, W, $R_1$, $R_2$ and $R_3$ have the same meanings as defined above, is dehalogenated in the presence of a catalyst under hydrogen to obtain a benzene derivative represented by the formula (I):

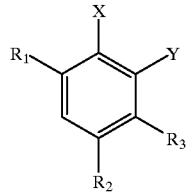

wherein X, Y, $R_1$, $R_2$ and $R_3$ have the same meanings as defined above.

As the catalyst, there may be used platinum group element such as platinum, palladium, osmium, iridium, ruthenium, rhodium, etc., and it's salt with mineral acid such as hydrochloride, but preferably platinum and palladium. The platinum group element and their salt with mineral acid such as hydrochloride may be supported on a carrier such as activated charcoal, graphite, silica, alumina, silica-alumina, zeolite, zirconia, diatomaceous earth, barium sulfate, etc., but preferably carbon. The catalyst may be used in a stoichiometrical amount or 0.001 to 20 times the stoichiometrical amount, but preferably a stoichiometrical amount or 0.05 to five times the stoichiometrical amount.

The reaction can be carried out under the range from atmospheric pressure to 2000 kPa, but preferably under the range from atmospheric pressure to 1000 kPa.

As the solvent, any solvent inert to a reactant and a catalyst may be used. There may be mentioned aliphatic alcohols such as methanol, ethanol, etc., aromatic hydrocarbons such as toluene, xylene, etc., esters such as ethyl acetate, butyl acetate, methyl benzoate, etc., ethers such as tetrahydrofuran, etc., organic acids such as acetic acid, etc., and water, but preferably aliphatic alcohols, ethers organic acids and water. A mixture of the solvents which are described above may be used.

The reaction can be carried out at a temperature from 0° C. to the boiling point of the solvent, but preferably in the range from 20° C. to the boiling point of the solvent.

As a scavenger of acid which is generated in the course of the reaction, there may be used alkaline metal hydroxide such as potassium hydroxide, sodium hydroxide, etc., alkaline metal carbonate such as potassium carbonate, sodium carbonate, etc., alkaline metal alkoxide such as sodium methoxide, sodium ethoxide, potassium t-butoxide, etc., and organic base such as pyridine, triethylamine, etc.

The third process is summarized in the scheme 3 as shown below.

Scheme 3

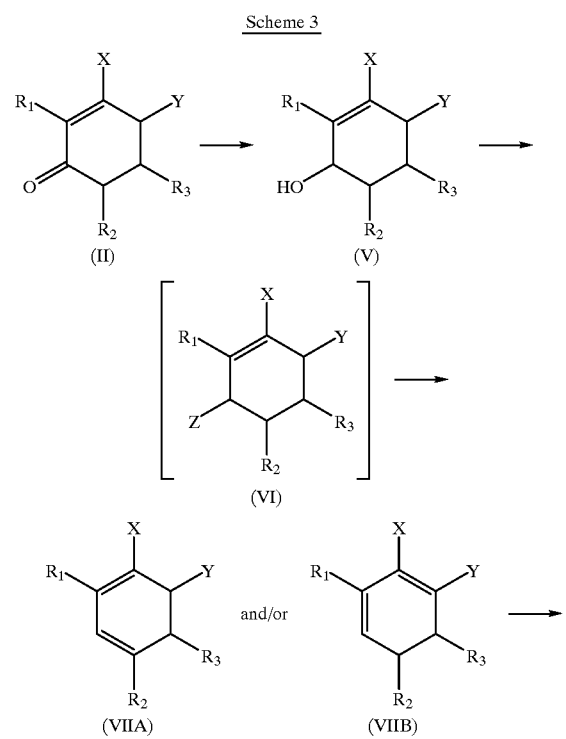

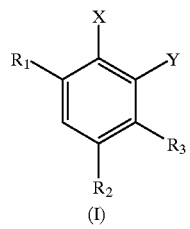

(I)

A cyclohexenone derivative represented by the formula (II):

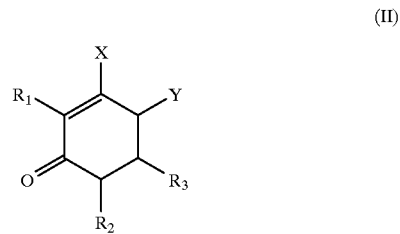

wherein X, Y, R₁, R₂ and R₃ have the same meanings as defined above, is reacted with a reducing agent in a solvent to obtain a cyclohexenol derivative of the formula (V):

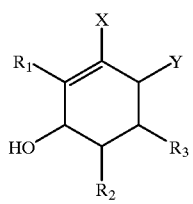

wherein X, Y, R₁, R₂ and R₃ have the same meanings as defined above.

As the reducing agent, borohydride or aluminum hydride reagents may be used. There may be mentioned borohydrides such as sodium borohydride, sodium cyanoborohydride, etc., aluminum hydrides such as lithium aluminum hydrides, etc., but preferably borohydrides.

The reducing agent may be used in a stoichiometrical amount or 0.2 to five times the stoichiometrical amount, but preferably a stoichiometrical amount or 0.25 to four times the stoichiometrical amount.

If necessary, there may be used inorganic salt such as cerium chloride as the additive.

As the solvent, any solvent inert to a reactant and a reagent may be used. There may be mentioned aliphatic alcohols such as methanol, ethanol, etc., aromatic hydrocarbons such as toluene, xylene, etc., ethers such as tetrahydrofuran, etc., and water, but preferably aliphatic alcohols, ethers and water. A mixture of the solvents which are described above may be used.

The reaction can be carried out at a temperature from −40° C. to the boiling point of the solvent., but preferably in the range from −20° C. to 40° C.

A cyclohexenol derivative represented by the formula (V):

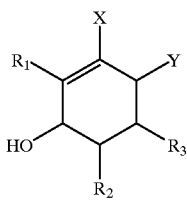

wherein X, Y, R$_1$, R$_2$ and R$_3$ have the same meanings as defined above, is reacted with a dehydrating agent in a solvent to obtain a cyclohexadiene derivative or a mixture of isomers represented by the formula (VIIA and/or VIIB):

(VIIA and/or VIIB)

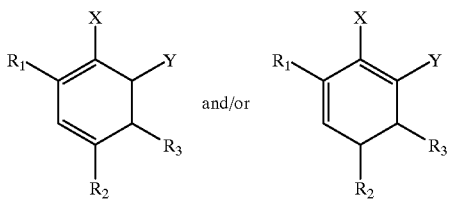

wherein X, Y, R$_1$, R$_2$ and R$_3$ have the same meanings as defined above.

Any ratio of the isomers (IIIA and IIIB) may be employed.

As the dehydrating agent, there may be used inorganic acids such as hydrochloric acid, sulfuric acid, boric acid, etc., inorganic salts such as potassium hydrogen sulfate, iron(II) sulfate, etc., sulfonic acid such as p-toluenesulfonic acid, methanesulfonic acid, trifluoromethanesulfonic acid, etc., silica and alumina, but preferably sulfuric acid, potassium hydrogen sulfate and iron(II) sulfate on silica gel. A mixed agent of the above also may be used. The dehydrating agent may be used in a stoichiometrical amount or 0.01 to 10 times the stoichiometrical amount, but preferably a stoichiometrical amount or 0.1 to five times the stoichiometrical amount.

As the solvent, any solvent inert to a reactant and a reagent may be used. There may be mentioned aliphatic alcohol such as methanol, ethanol, etc., aliphatic hydrocarbons such as n-hexane, n-heptane, etc., aromatic hydrocarbons such as toluene, xylene, etc., halogenated hydrocarbons such as dichloromethane, chlorobenzene, etc., ethers such as tetrahydrofuran, etc., and water, but preferably aliphatic alcohols, aliphatic hydrocarbons, aromatic hydrocarbons, halogenated hydrocarbons and water. A mixed solvent of the above may be used. And this step may be carried out without a solvent.

The reaction can be carried out at a temperature from –20° C. to 400° C., but preferably in the range from 0° C. to 300° C. or the boiling point of the solvent. And in this step as the dehydrating agent, chlorinating agents, brominating agents, acylating agents and sulfonylating agents may be used. There may be used chlorinating agents such as thionyl chloride, phosgen, oxalyl chloride, phosphorus oxychloride, phosphorus pentachloride, etc., brominating agents such as thionyl bromide, phosphorus oxybromide, etc., acylating agents such as acetyl chloride, acetic anhydride, etc., sulfonylating agents such as p-toluenesulfonyl chloride, methanesulfonyl chloride, trifluoromethanesulfonic anhydride, etc., but preferably chlorinating agents. The agent may be used in a stoichiometrical amount or 0.5 to 10 times the stoichiometrical amount, but preferably a stoichiometrical amount or 0.8 to five times the stoichiometrical amount.

If necessary, a base may be used in this step. There may be used alkaline metal hydroxides such as potassium hydroxide, sodium hydroxide, etc., alkaline metal carbonates such as potassium carbonate, sodium carbonate, etc., alkaline metal alkoxides such as sodium methoxide, sodium ethoxide, potassium t-butoxide, etc., alkaline metal hydrides such as sodium hydride etc. and organic bases such as pyridine, triethylamine, etc., but preferably alkaline metal carbonates, alkaline metal alkoxides and organic bases. The base may be used in a stoichiometrical amount or 0.5 to 20 times the stoichiometrical amount, but preferably a stoichiometrical amount or 0.8 to 10 times the stoichiometrical amount.

As the solvent, any solvent inert to a reactant and a reagent may be used. There may be mentioned aliphatic hydrocarbons such as n-hexane, n-heptane, etc., aromatic hydrocarbons such as toluene, xylene, etc., halogenated hydrocarbons such as dichloromethane, chlorobenzene, etc., ethers such as tetrahydrofuran, etc., esters such as ethyl acetate, butyl acetate, etc., but preferably aliphatic hydrocarbons, aromatic hydrocarbons, ethers and esters. A mixture of the solvents which are described above may be used.

And this step may be carried out without a solvent.

The reaction can be carried out at a temperature from –30° C. to the boiling point of the solvent, but preferably in the range from –10° C. to the boiling point of the solvent.

In this step, a cyclohexene derivative represented by the formula (VI):

(VI)

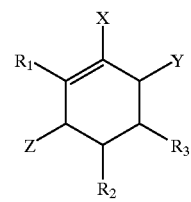

wherein X, Y, R$_1$, R$_2$ and R$_3$ have the same meanings as defined above and Z represents halogen, a (C$_1$–C$_6$)acyloxy group, a (C$_1$–C$_6$)alkoxycarbonyloxy group, a N,N-di(C$_1$–C$_4$)alkylcarbamoyloxy group, a (C$_1$–C$_6$) alkylsulfonyloxy group, a benzenesulfonyl group which is optionally substituted with (C$_1$–C$_4$)alkyl group(s), (C$_1$–C$_4$) alkoxy group(s), halogen atom(s), may be isolated as an intermediate. It may be reacted with the base described above to obtain a cyclohexadiene derivative or a mixture of isomers represented by the formula (VIIA and/or VIIB):

(VIIA and/or VIIB)

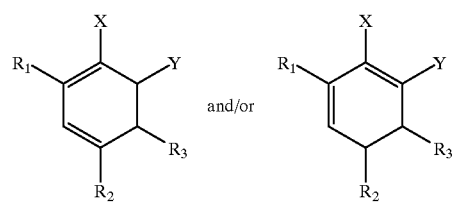

wherein X, Y, R$_1$, R$_2$ and R$_3$ have the same meanings as defined above.

Any ratio of the isomers (IIIA and IIIB) may be employed.

A cyclohexadiene derivative or a mixture of isomers represented by the formula (VIIA and/or VIIB):

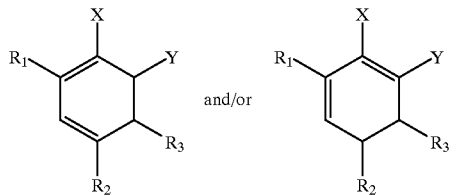

(VIIA and/or VIIB)

wherein X, Y, $R_1$, $R_2$ and $R_3$ have the same meanings as defined above, is reacted with a dehydrogenating agent in a solvent to obtain a halobenzene derivative of the formula (I):

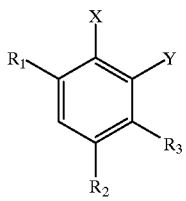

(I)

wherein X, Y, $R_1$, $R_2$ and $R_3$ have the same meanings as defined above.

As the dehydrogenating agent, oxidizing agent and base may be used. There may be mentioned oxidizing agent such as metal oxides(potassium permanganate, etc.), platinum group metals(platinum, palladium, osmium, iridium, ruthenium, rhodium, etc.) and it's salts with mineral acids such as hydrochloride, halogenating agent(thionyl chloride, sulfulyl chloride, etc.), quinones(DDQ, etc.), sulfur. The platinum group metals and it's salts with mineral acids such as hydrochloride may be supported on a carrier such as activated charcoal, graphite, silica, alumina, silica-alumina, zeolite, zirconia, diatomaceous earth, barium sulfate, etc. The oxidizing agent may be used in a stoichiometrical amount or 0.001 to 20 times the stoichiometrical amount, but preferably a stoichiometrical amount or 0.05 to 10 times the stoichiometrical amount. The reaction may be run under high concentration of oxygen. These agents may be used with oxygen.

As the base, there may be used alkaline metal hydroxide such as potassium hydroxide, sodium hydroxide, etc., alkaline metal carbonate such as potassium carbonate, sodium carbonate, etc., alkaline metal alkoxide such as sodium methoxide, sodium ethoxide, potassium t-butoxide, etc., alkaline metal hydrides such as sodium hydride etc., but preferred alkaline metal alkoxides. The base may be used in a stoichiometrical amount or 0.5 to 20 times the stoichiometrical amount, but preferably a stoichiometrical amount or 0.8 to 10 times the stoichiometrical amount.

As the solvent, any solvent inert to a reactant and a reagent may be used. There may be mentioned aliphatic alcohols such as methanol, ethanol, etc., aromatic hydrocarbons such as toluene, xylene, etc., aliphatic hydrocarbons such as n-hexane, n-heptane, etc., halogenated hydrocarbons such as dichloromethane, 1,2-dichloroethane, chlorobenzene, etc., esters such as ethyl acetate, butyl acetate, methyl benzoate, etc., ethers such as tetrahydrofuran, etc., nitriles such as acetonitrile etc., organic acids such as acetic acid, etc., and water, but preferably aliphatic hydrocarbons, aromatic hydrocarbons, halogenated hydrocarbons, ethers, nitriles, organic acids and water. A mixed solvent of the above also may be used.

The reaction can be carried out at a temperature from 20 to 400° C., but preferably in the range from 50° C. to 300° C.

All intermediates and products in the reaction steps described above can be recovered and isolated by conventional means such as extraction, etc. And they can be purified by conventional means such as recrystallization, distillation, column chromatography, etc.

In the formulas above, the general terms bear their usual meanings. For example, the heteroaromatic group may include furan, thiophene, pyrazole, isothiazole, imidazole, oxazole, thiazole, pyridine, pyridazine, pyrimidine, pyrazine, indole, benzo[b]furan, benzor[b]thiophene, benzo[d]imidazole, benzo[d]thiazole, purine, quinoline, isoquinoline, cinnoline, phtalazine, quinazoline, quinoxaline and pteridine; the halogen atom may include fluorine atom, chlorine atom, bromine atom and iodine atom; the ($C_1$–$C_4$) alkyl group may include methyl, ethyl, n-propyl, isopropyl, n-butyl, isobutyl and t-butyl; the ($C_1$–$C_4$)alkoxy group may include methoxy, ethoxy, n-propoxy, isopropoxy, n-butoxy, sec-butoxy, isobutoxy and t-butoxy; the ($C_1$–$C_4$) alkoxycarbonyl group may include methoxycarbonyl, ethoxycarbonyl, n-propoxycarbonyl, isopropoxycarbonyl, n-butoxycarbonyl, sec-butoxycarbonyl, isobutoxycarbonyl and t-butoxycarbonyl.

The following group of representative products and intermediates of the process and of this invention will be mentioned, to assure that the reader fully understands the overall purpose of the present process: as an example of a benzene derivative represented by the formula (I), methyl 2-phenylbenzoate, methyl 2-(4-methylphenyl)benzoate, ethyl 2-phenylbenzoate, ethyl 2-(2-methylphenyl)benzoate, ethyl 2-(4-methyphenyl)benzoate, ethyl 2-(4-methoxyphenyl)benzoate, ethyl 2-(4-nitrophenyl)benzoate, 2-phenylbenzenecarbonitrile, 2-(4-methylphenyl) benzenecarbonitrile, ethyl 2-(2-pyridyl)benzoate, ethyl 2-(3-pyridyl)benzoate, ethyl 2-(4-pyridyl)benzoate; as an example of a cyclohexenone derivative represented by the formula (II), methyl 4-oxo-2-phenylcyclohex-2-enecarboxylate, methyl 2-(4-methylphenyl)-4-oxocyclohex-2-enecarboxylate, ethyl 4-oxo-2-phenylcyclohex-2-enecarboxylate, ethyl 2-(2-methylphenyl)-4-oxocyclohex-2-enecarboxylate, ethyl 2-(4-methylphenyl)-4-oxocyclohex-2-enecarboxylate, ethyl 2-(4-methoxylphenyl)-4-oxocyclohex-2-enecarboxylate, ethyl 2-(4-nitrophenyl)-4-oxocyclohex-2-enecarboxylate, 4-oxo-2-phenylcyclohex-2-enecarbonitrile, 2-(4-methylphenyl)-4-oxocyclohex-2-enecarbonitrile, ethyl 4-oxo-2-(2-pyridyl)cyclohex-2-enecarboxylate, ethyl 4-oxo-2-(3-pyridyl)cyclohex-2-enecarboxylate, ethyl 4-oxo-2-(4-pyridyl)cyclohex-2-enecarboxylate, as an example of a halocyclohexadiene derivative represented by the formula (IIIA), methyl 4-chloro-2-phenylcyclohexa-2,4-dienecarboxylate, methyl 4-chloro-2-(4-methylphenyl)cyclohexa-2,4-dienecarboxylate, ethyl 4-chloro-2-phenylcyclohexa-2,4-dienecarboxylate, ethyl 4-chloro-2-(2-methylphenyl) cyclohexa-2,4-dienecarboxylate, ethyl 4-chloro-2-(4-methylphenyl)cyclohexa-2,4-dienecarboxylate, ethyl 4-chloro-2-(4-methoxylphenyl)cyclohexa-2,4-dienecarboxylate, ethyl 4-chloro-2-(4-nitrophenyl) cyclohexa-2,4-dienecarboxylate, 4-chloro-2-phenylcyclohexa-2,4-dienecarbonitrile, 4-chloro-2-(4- methylphenyl)cyclohexa-2,4-dienecarbonitrile, ethyl 4-chloro-2-(2-pyridyl)cyclohexa-2,4-dienecarboxylate, ethyl 4-chloro-2-(3-pyridyl)cyclohexa-2,4-dienecarboxylate, ethyl 4-chloro-2-(4-pyridyl)cyclohexa-2,4-dienecarboxylate; as an example of a halocyclohexadiene derivative represented by the formula (IIIB), methyl 4-chloro-2-phenylcyclohexa-1,3-dienecarboxylate, methyl 4-chloro-2-(4-methylphenyl)cyclohexa-1,3-dienecarboxylate, ethyl 4-chloro-2-phenylcyclohexa-1,3-dienecarboxylate, ethyl 4-chloro-2-(2-methyphenyl)cyclohexa-1,3-dienecarboxylate, ethyl 4-chloro-2-(4-methylphenyl)cyclohexa-1,3-dienecarboxylate, ethyl 4-chloro-2-(4-methoxylphenyl)cyclohexa-1,3-dienecarboxylate, ethyl 4-chloro-2-(4-nitrophenyl)cyclohexa-1,3-dienecarboxylate, 4-chloro-2-phenylcyclohexa-1,3-dienecarbonitrile, 4-chloro-2-(4-methylphenyl)cyclohexa-1,3-dienecarbonitrile, ethyl 4-chloro-2-(2-pyridyl)cyclohexa-1,3-dienecarboxylate, ethyl 4-chloro-2-(3-pyridyl)cyclohexa-1,3-dienecarboxylate, ethyl 4-chloro-2-(4-pyridyl)cyclohexa-1,3-dienecarboxylate; as an example of a halobenzene derivative represented by the formula (IV), methyl 3-chloro-2-phenylbenzoate, methyl 3-chloro-2-(4-methylphenyl)benzoate, ethyl 3-chloro-2-phenylbenzoate, ethyl 3-chloro-2-(2-methylphenyl)benzoate, ethyl 3-chloro-2-(4-methylphenyl)benzoate, ethyl 3-chloro-2-(4-methoxylphenyl)benzoate, ethyl 3-chloro-2-(4-nitrophenyl)benzoate, 3-chloro-2-phenylbenzenecarbonitrile, 3-chloro-2-(4-methylphenyl)benzenecarbonitrile, ethyl 3-chloro-2-(2-pyridyl)benzoate, ethyl 3-chloro-2-(3-pyridyl)benzoate, ethyl 3-chloro-2-(4-pyridyl)benzoate; as an example of a cyclohexenol derivative represented by the formula (V), methyl 4-hydroxy-2-phenylcyclohex-2-enecarboxylate, methyl 4-hydroxy-2-(4-methylphenyl)cyclohex-2-enecarboxylate, ethyl 4-hydroxy-2-phenylcyclohex-2-enecarboxylate, ethyl 4-hydroxy-2-(2-methylphenyl)cyclohex-2-enecarboxylate, ethyl 4-hydroxy-2-(4-methylphenyl)cyclohex-2-enecarboxylate, ethyl 4-hydroxy-2-(4-methoxylphenyl)cyclohex-2-enecarboxylate, ethyl 4-hydroxy-2-(4-nitrophenyl)-cyclohex-2-enecarboxylate, 4-hydroxy-2-phenylcyclohex-2-enecarbonitrile, 4-hydroxy-2-(4-methylphenyl)cyclohex-2-enecarbonitrile, ethyl 4-hydroxy-2-(2-pyridyl)cyclohex-2-enecarboxylate, ethyl 4-hydroxy-2-(3-pyridyl)cyclohex-2-enecarboxylate, ethyl 4-hydroxy-2-(4-pyridyl)cyclohex-2-enecarboxylate, as an example of a cyclohexenol derivative represented by the formula (VI), methyl 4-chloro-2-phenylcyclohex-2-enecarboxylate, methyl 4-chloro-2-(4-methylphenyl)cyclohex-2-enecarboxylate, ethyl 4-chloro-2-phenylcyclohex-2-enecarboxylate, ethyl 4-chloro-2-(2-methylphenyl)cyclohex-2-enecarboxylate, ethyl 4-chloro-2-(4-methylphenyl)cyclohex-2-enecarboxylate, ethyl 4-chloro-2-(4-methoxylphenyl)cyclohex-2-enecarboxylate, ethyl 4-chloro-2-(4-nitrophenyl)-cyclohex-2-enecarboxylate, 4-chloro-2-phenylcyclohex-2-enecarbonitrile, 4-chloro-2-(4-methylphenyl)cyclohex-2-enecarbonitrile, ethyl 4-chloro-2-(2-pyridyl)cyclohex-2-enecarboxylate, ethyl 4-chloro-2-(3-pyridyl)cyclohex-2-enecarboxylate, ethyl 4-chloro-2-(4-pyridyl)cyclohex-2-enecarboxylate, ethyl 4-methanesulfonyloxy-2-phenylcyclohex-2-enecarboxylate, ethyl 4-methanesulfonyloxy-2-(2-methylphenyl)cyclohex-2-enecarboxylate, ethyl 4-methanesulfonyloxy-2-(4-methylphenyl)cyclohex-2-enecarboxylate, ethyl 4-methanesulfonyloxy-2-(4-nitrophenyl)-cyclohex-2-enecarboxylate, 4-methanesulfonyloxy-2-phenylcyclohex-2-enecarbonitrile, 4-methanesulfonyloxy-2-(4-methylphenyl)cyclohex-2-enecarbonitrile, ethyl 4-acetoxy-2-phenylcyclohex-2-enecarboxylate, ethyl 4-acetoxy-2-(2-methylphenyl)cyclohex-2-enecarboxylate, ethyl 4-acetoxy-2-(4-methylphenyl)cyclohex-2-enecarboxylate, ethyl 4-acetoxy-2-(4-nitrophenyl)-cyclohex-2-enecarboxylate, 4-acetoxy-2-phenylcyclohex-2-enecarbonitrile, 4-acetoxy-2-(4-methylphenyl)cyclohex-2-enecarbonitrile; as an example of a cyclohexadiene derivative represented by the formula (VIIA), methyl 2-phenylcyclohexa-2,4-dienecarboxylate, methyl 2-(4-methylphenyl)cyclohexa-2,4-dienecarboxylate, ethyl 2-phenylcyclohexa-2,4-dienecarboxylate, ethyl 2-(2-methylphenyl)cyclohexa-2,4-dienecarboxylate, ethyl 2-(4-methylphenyl)cyclohexa-2,4-dienecarboxylate, ethyl 2-(4-methoxylphenyl)cyclohexa-2,4-dienecarboxylate, ethyl 2-(4-nitrophenyl)cyclohexa-2,4-dienecarboxylate, 2-phenylcyclohexa-2,4-dienecarbonitrile, 2-(4-methylphenyl)cyclohexa-2,4-dienecarbonitrile, ethyl 2-(2-pyridyl)cyclohexa-2,4-dienecarboxylate, ethyl 2-(3-pyridyl)cyclohexa-2,4-dienecarboxylate, ethyl 2-(4-pyridyl)cyclohexa-2,4-dienecarboxylate; as an example of a cyclohexadiene derivative represented by the formula (VIIA), methyl 2-phenylcyclohexa-1,3-dienecarboxylate, methyl 2-(4-methylphenyl)cyclohexa-1,3-dienecarboxylate, ethyl 2-phenylcyclohexa-1,3-dienecarboxylate, ethyl 2-(2-methylphenyl)cyclohexa-1,3-dienecarboxylate, ethyl 2-(4-methylphenyl)cyclohexa-1,3-dienecarboxylate, ethyl 2-(4-methoxylphenyl)cyclohexa-1,3-dienecarboxylate, ethyl 2-(4-nitrophenyl)cyclohexa-1,3-dienecarboxylate, 2-phenylcyclohexa-2,4-dienecarbonitrile. 2-(4-methylphenyl)cyclohexa-1,3-dienecarbonitrile, ethyl 2-(2-pyridyl)cyclohexa-1,3-dienecarboxylate, ethyl 2-(3-pyridyl)cyclohexa-1,3-dienecarboxylate, ethyl 2-(4-pyridyl)cyclohexa-1,3-dienecarboxylate.

This invention provides advantageous processes for (hetero)aromatic substituted benzene derivatives which are key intermediates for pharmaceuticals.

Angiotensin II receptor plays an important roll in the renin-angiotensin system (RAS) and it's selective inhibitors are developed as an antihypertensive agent. Losartan, Candesartan, Valsartan, Irbesartan, Olmesartan and Termisartan have been launched and have a common structure, biphenyl tetrazol and acid. The key intermediate, biphenyl tetrazol or acid, is derived from it's nitrile or ester derivative which is synthesized in this art.

YM087 and YM471, vasopressin antagonist, are under developed for heart failure. These agents also have a biphenyl amide structure which is derived from the biphenyl ester in this art.

The following examples further illustrate the manner in which this invention is carried out.

EXAMPLES

Preparation 1

Ethyl 2-((4-methylphenyl)carbonyl)-5-oxohexanoate

To a stirred solution of methyl 3-(4-methylphenyl)-3-oxopropanoate(2.28 g, 11.1 mmol) in EtOH(10 ml), NaOEt (11 mg, 0.16 mmol) was added and methyl vinyl ketone(2.0 g, 27.8 mmol) was added dropwise less than 25° C. After stirring the reaction mixture for 30 min. less than 25° C., the solvent was evaporated under reduced pressure. Dil.HCl aq. was added to the residue and extracted by EtOAc. The organic layer was washed with water and brine, dried over $MgSO_4$. After removal of the solvent, the residue was purified by column chromatography on silica gel with n-hexane-AcOEt to afford 2.73 g of ethyl 2-((4-methylphenyl)carbonyl)-5-oxohexanoate as a pale yellow oil (y=89.0%). $^1$H-NMR(ppm, 300 MHz, $CDCl_3$) δ 7.92(2H, d, J=8.0 Hz), 7.28(2H, d, J=8.0 Hz), 4.41(1H, t, J=7.0 Hz), 4.14(2H, q, J=6.9 Hz), 2.55–2.60(2H, m), 2.13(3H, s), 1.17(3H, t, J=6.9 Hz)

Preparation 2

Ethyl 2-(4-methylphenyl)-4-oxocyclohex-2-enecarboxylate

A mixture of 2-((4-methylphenyl)carbonyl)-5-oxohexanoate(4.19 g, 15.2 mmol), acetic acid(137 mg, 2.28 mmol) and piperidine(129 mg, 1.52 mmol) in toluene(10 ml) was refluxed for 9 hr. After cooling down to room temperature, AcOEt was added to the reaction mixture and washed with dil. HCl, water and brine, dried over $MgSO_4$. After removal of the solvent, the residue was purified by column chromatography on silica gel with n-hexane-AcOEt to afford 3.46 g of ethyl 2-(4-methylphenyl)-4-oxocyclohex-2-enecarboxylate(y=88.0%) as a brown oil. iH-NMR(ppm, 300 MHz, $CDCl_3$) δ 7.41(2H, d, J=8.2 Hz), 7.21(2H, d, J=8.2 Hz), 5.47(1H, s), 4.11(2H, q, J=7.0 Hz), 3.96(1H, dd, J=4.8 and 4.8 Hz), 2.55–2.65(1H, m), 2.40–2.55(3H, m), 2.38(3H, s), 1.14(3H, t, J=7.0 Hz)

Preparation 3

Ethyl 4-oxo-2-phenylcyclohex-2-enecarboxylate

A mixture of 2-(phenylcarbonyl)-5-oxohexanoate(3.87 g, 14.8 mmol), acetic acid(130 mg, 2.17 mmol) and piperidine (127 mg, 1.49 mmol) in toluene(5 ml) was refluxed for 5 hr. After cooling down to room temperature, AcOEt was added to the reaction mixture and washed with dil. HCl, water and brine and dried over $MgSO_4$. After removal of the solvent, the residue was purified by column chromatography on silica gel with n-hexane-AcOEt to afford 4.02 g of ethyl 4-oxo-2-phenylcyclohex-2-enecarboxylate(y=94.7%) as a brown oil. $^1$H-NMR(ppm, 30 MHz, $CDCl_3$) δ 7.50(2H, dd, J=3.0 and 6.4 Hz), 7.40–7.48(3H), 6.47(1H, s), 4.11(2H, q, J=7.0 Hz), 3.96(1H, dd, J=3.7 and 3.7 Hz), 2.60–2.70(1H, m), 2.35–2.55(3H), 1.12(3H, t, J=7.0 Hz)

Example 1

Ethyl 4-chloro-2-phenylcyclohexa-2,4-dienecarboxylate and Ethyl 4-chloro-2-phenylcyclohexa-1,3-dienecarboxylate To a stirred solution of 2-(4-methylphenyl)-4-oxocyclohex-2-enecarboxylate(1.24 g, 5.1 mmol) in toluene (10 ml) was added oxalyl chloride(2.58 g, 20.4 mmol). After stirring for 2 hr. at 70–75° C., AcOEt was added to the reaction mixture and washed with water, sat.NaHCO3 and brine, dried over $MgSO_4$. Concentration afford 1.24 g of ethyl 4-chloro-2-phenylcyclohexa-2,4-dienecarboxylate and ethyl 4-chloro-2-phenylcyclohexa-3-dienecarboxylate(y=93.0%) as a pale yellow oil. This product was used at next step without purification. $^1$H-NMR(ppm, 300 MHz, $CDCl_3$) δ 7.25–7.45(8H), 7.13–7.16(2H), 6.35(1H, s), 6.19(1H, s), 5.87(1H, brs), 4.09(2H, q, J=7.3 Hz), 3.93(2H, q, J=7.3 Hz), 3.64(1H, dd, J=3.8 and 8.6 Hz), 2.90–3.05(1H, m), 2.60–2.85(5H), 1.34(3H, t, J=7.3 Hz), 0.89(3H, t, J=7.3 Hz)

Example 2

Ethyl 4-chloro-2-phenylbenzoate

To a stirred solution of ethyl 4-chloro-2-phenylcyclohexa-2,4-dienecarboxylate and ethyl 4-chloro-2-phenylcyclohexa-1,3-dienecarboxylate(200 mg, 0.762 mmol) in tert-BuOH(3 ml), tert-BuOK(103 mg, 0.914 mmol) was added by portion on a water bath. After stirring for 2 days, water was added to the reaction mixture and it was acidified with dil. HCl aq., extracted with AcOEt. The organic layer was washed with brine and dried over $MgSO_4$. Concentration of the organic layer afford a mixture(200 mg) of ethyl 4-chloro-2-phenylbenzoate and 4-chloro-2-phenylbenzoic acid. $^1$H-NMR(ppm, 300 MHz, $CDCl_3$) δ ester 7.79(1H, d, J=8.0 Hz), 7.10–7.50(7H), 4.07(2H, d, J=6.9 Hz), 0.98(3H, t, J=6.9 Hz); acid 7.91(1H, d, J=8.7 Hz)

Example 3

Ethyl 4-hydroxy-2-phenylcyclohex-2-enecarboxylate

To a stirred solution of ethyl 4-oxo-2-phenylcyclohex-2-enecarboxylate(500 mg, 2.05 mmol) in MeOH(10 ml) at 0° C., $NaBH_4$ (77.5 mg, 2.05 mmol) was added by portions. After stirring for 45 minutes, dil.HCl aq. was added to the reaction mixture and the solvent was evaporated under reduced pressure. The residue was added water and extracted with AcOEt. The organic layer was washed with water and brine, dried over $MgSO_4$. Concentration of the organic layer afford 504 mg of ethyl 4-hydroxy-2-phenylcyclohex-2-enecarboxylate(y=100%) as a pale yellow crystal. $^1$H-NMR(ppm, 300 MHz, $CDCl_3$) δ 7.23–7.34 (5H, m), 6.10–6.22(1H, m), 4.30–4.50(1H, m), 3.90–4.08 (1H, m), 3.72 and 3.64(1H, t and t, J=5.8 and 5.3 Hz), 1.60–2.30(4H, m), 1.00 and 1.10(3H, m)

Example 4

Ethyl 4-chloro-2-phenylcyclohex-2-enecarboxylate

To a stirred solution of ethyl 4-hydroxy-2-phenylcyclohex-2-enecarboxylate (10 mg, 0.407 mmol) in toluene(2 ml) was added thionyl chloride(0.074 ml, 1.02 mmol) at 5° C. After stirring for 3 hr. at room temperature. AcOEt was added to the reaction mixture and it was washed with water, sat.NaHCO$_3$ aq. and brine, dried over $MgSO_4$. Concentration of the organic layer afford 110 mg of ethyl 4-chloro-2-phenylcyclohex-2-enecarboxylate(y=100%) as a pale yellow oil. $^1$H-NMR(ppm, 300 MHz, $CDCl_3$) δ 7.25–7.37(5H, m), 6.27 and 6.18(1H, d and t, J=4.6 and 1.7 Hz), 4.87–4.91 and 4.74–4.79(1H, m), 4.03 and 3.96(2H, q, J=6.9 and 7.1 Hz), 3.68–3.76(1H, m), 2.05–2.37(4H, m), 1.09 and 0.97(3H, t, J=6.9 and 7.1 Hz)

Example 5

Ethyl 2-phenylcyclohexa-2,4-dienecarboxylate

A mixture of 4-hydroxy-2-phenylcyclohex-2-enecarboxylate(680 mg, 2.61 mmol) and $FeSO_4$, which had been activated on silica gel, in $CH_2Cl_2$ (6 ml)was stirred at 45° C. for 1 hr. After filtration, the filtrate was concentrated to give a residue which was purified by column chromatography on silica gel with n-hexane-AcOEt to afford 275 mg of ethyl 2-phenylcyclohexa-2,4-dienecarboxylate(43.5%). $^1$H-NMR(ppm, 300 MHz, CDCl3) δ 7.32(2H, d, J=8.2 Hz), 7.13(2H, d, J=8.2 Hz), 6.43(1H, d, J=5.5 Hz), 6.12(1H, m), 5.85(1H, m)4.08(2H, q, J=7.1 Hz), 3.61(1H, dd, J=8.9 and 3.3), 2.86(1H, ddd, 17.7, 5.3, 3.3 Hz), 2.61(1H, dddd, J=17.7, 8.9, 2.9, 2.9 Hz), 2.34(3H, s), 1.14(3H, t, J=7.1 Hz)

Example 6

Ethyl 2-phenylcyclohexa-1,3-dienecarboxylate

To a stirred solution of ethyl 4-chloro-2-phenylcyclohex-2-enecarboxylate (110 mg, 0.407 mmol) in tert-BuOH(2 ml), tert-BuOK(93 mg, 0.832 mmol) was added by portion on a water bath. After stirring for 1 hr. at room temperature, water was added to the reaction mixture, and it was acidified with dil. HCl aq. and extracted with AcOEt. The organic layer was washed with brine and dried over $MgSO_4$. After removal of the solvent, the residue was purified by column chromatography on silica gel with n-hexane-AcOEt to afford 70 mg of ethyl 2-phenylcyclohexa-1,3-dienecarboxylate (y=74.0%) as a pale yellow oil. $^1$H-NMR(ppm, 300 MHz, CDCl$_3$) δ 7.14–7.39(5H, m), 6.03–6.24(2H, m), 3.94(2H, q, J=6.9 Hz), 2.55–2.65(2H, m), 2.26–2.35(2H, m), 0.90(3H, t, J=6.9 Hz)

Example 7

Ethyl 2-phenylbenzoate

1) To a stirred solution of a mixture(620 mg, 2.54 mmol) of ethyl 4-chloro-2-phenylcyclohexa-2,4-dienecarboxylate and ethyl 4-chloro-2-phenylcyclohexa-1,3-dienecarboxylate in MeOH(5 ml), NaOMe(28% in MeOH, 1.98 g, 10.1 mmol) was added. After stirring for 17 hr at room temperature, the solvent was evaporated under reduced pressure. Water was added to the residue and dil. HCl aq., and it was extracted with AcOEt. The organic layer was washed with brine and dried over MgSO$_4$. After removal of the solvent, the residue was purified by column chromatography on silica gel with n-hexane-AcOEt to afford 136 mg of ethyl 2-phenylbenzoate(y=23.7%) and 236 mg of 2-phenylbenzoic acid(y=53.8%). $^1$H-NMR(ppm, 300 MHz, CDCl$_3$) δ ester 7.82(1H, dd, J=1.4 and 7.7 Hz), 7.10–7.60(8H), 4.08(2H, d, J=7.0 Hz), 0.98(3H, t, J=7.0 Hz); acid 7.95(1H, d, J=7.9 Hz)

2) A mixture of ethyl 4-chloro-2-phenylbenzoate and 4-chloro-2-phenylbenzoic acid(200 mg) and 5%Pd/C (200 mg) in EtOH(10 ml) was vigorously stirred under 300 kPa of H$_2$ at room temperature for 2 days. After filtration, the filtrate was concentrated to give a mixture of ethyl 2-phenylbenzoate and 2-phenylbenzoic acid. $^1$H-NMR(ppm, 300 MHz, CDCl$_3$) δ ester 7.82(1H, dd, J=1.4 and 7.7 Hz), 7.10–7.60(8H), 4.08(2H, d, J=7.0 Hz), 0.98(3H, t, J=7.0 Hz); acid 7.95(1H, d, J=7.9 Hz)

3) A mixture of ethyl 2-phenylcyclohexa-1,3-dienecarboxylate(90 mg, 0.395 mmol) and 5%Pd/C(50 mg) in acetic acid(1.5 ml) and water(1.5 ml) was refluxed for 2 hr. The reaction mixture was filtrated and the solvent was evaporated under reduced pressure. Toluene was added to the residue and it was dried over MgSO$_4$. After removal of the solvent, the residue was purified by column chromatography on silica gel with n-hexane-AcOEt to afford 71 mg of ethyl 2-phenylbenzoate(y=80.0%) as a pale yellow oil. $^1$H-NMR(ppm, 300 MHz, CDCl$_3$) δ 7.82(1H, dd, J=1.4 and 7.7 Hz), 7.10–7.60(8H), 4.08(2H, d, J=7.0 Hz), 0.98(3H, t, J=7.0 Hz)

4) A mixture of ethyl 2-(4-methylphenyl)cyclohexa-2,4-dienecarboxylate(275 mg, 1.13 mmol) and activated MnO$_2$(491 mg, 5.65 mmol) in dichloroethane(5 ml) was refluxed for 4 hr. After filtration, the filtrate was concentrated to give a residue which was purified by column chromatography on silica gel with n-hexane-AcOEt to afford 265 mg of 2-(4-methylphenyl) benzoate(y=97.5%) as a pale yellow oil. $^1$H-NMR (ppm, 300 MHz, CDCl$_3$) δ 7.82(1H, dd, J=1.4 and 7.7 Hz), 7.10–7.60(8H), 4.08(2H, d, J=7.0 Hz), 0.98(3H, t, J=7.0 Hz)

What is claimed is:

1. A process for preparing a benzene derivative represented by the formula (I):

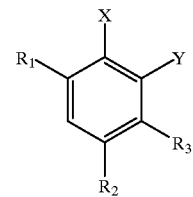

(I)

wherein X represents a phenyl group, a naphthyl group or a heteroaromatic group which are optionally substituted with (C$_1$–C$_4$)alkyl group(s), (C$_1$–C$_4$)alkoxy group(s), halogen atom(s) or nitro group(s); Y represents a (C$_1$–C$_4$) alkoxycarbonyl group, a cyano group, a nitro group or a (C$_1$–C$_4$)alkoxysulfonyl group; R$_1$, R$_2$ and R$_3$ each independently represent a hydrogen atom, a (C$_1$–C$_4$)alkyl group, a (C$_1$–C$_4$)alkoxy group or a phenyl group which is optionally substituted with (C$_1$–C$_4$)alkyl group(s), (C$_1$–C$_4$)alkoxy group(s) or halogen atom(s); which comprises aromatizing a cyclohexenone derivative represented by the formula (II):

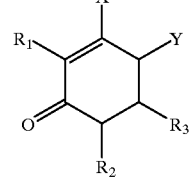

(II)

wherein X represents a phenyl group, a naphthyl group or a heteroaromatic group which are optionally substituted with (C$_1$–C$_4$)alkyl group(s), (C$_1$–C$_4$)alkoxy group(s), halogen atom(s) or nitro group(s); Y represents a (C$_1$–C$_4$) alkoxycarbonyl group, a cyano group, a nitro group or a (C$_1$–C$_4$)alkoxysulfonyl group; R$_1$, R$_2$ and R$_3$ each independently represent a hydrogen atom, a (C$_1$–C$_4$)alkyl group, a (C$_1$–C$_4$)alkoxy group or a phenyl group which is optionally substituted with (C$_1$–C$_4$)alkyl group(s), (C$_1$–C$_4$)alkoxy group(s) or halogen atom(s).

2. A process for preparing a benzene derivative represented by the formula (I):

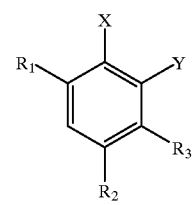

(I)

wherein X represents a phenyl group, a naphthyl group or a heteroaromatic group which are optionally substituted with (C$_1$–C$_4$)alkyl group(s), (C$_1$–C$_4$)alkoxy group(s), halogen atom(s) or nitro group(s); Y represents a (C$_1$–C$_4$) alkoxycarbonyl group, a cyano group, a nitro group or a (C$_1$–C$_4$)alkoxysulfonyl group; R$_1$, R$_2$ and R$_3$ each independently represent a hydrogen atom, a (C$_1$–C$_4$)alkyl group, a (C$_1$–C$_4$)alkoxy group or a phenyl group which is optionally substituted with (C$_1$–C$_4$)alkyl group(s), (C$_1$–C$_4$)alkoxy group(s) or halogen atom(s); which comprises halogenating a cyclohexenone derivative represented by the formula (II):

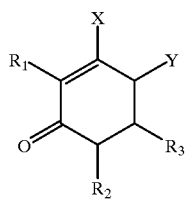

wherein X represents a phenyl group, a naphthyl group or a heteroaromatic group which are optionally substituted with $(C_1-C_4)$alkyl group(s), $(C_1-C_4)$alkoxy group(s), halogen atom(s) or nitro group(s); Y represents a $(C_1-C_4)$ alkoxycarbonyl group, a cyano group, a nitro group or a $(C_1-C_4)$alkoxysulfonyl group; $R_1$, $R_2$ and $R_3$ each independently represent a hydrogen atom, a $(C_1-C_4)$alkyl group, a $(C_1-C_4)$alkoxy group or a phenyl group which is optionally substituted with $(C_1-C_4)$alkyl group(s), $(C_1-C_4)$alkoxy group(s) or halogen atom(s), to obtain a chlorocyclohexadiene derivative or a mixture of isomers represented by the formula (IIIA and/or IIIB):

(IIIA and/or IIIB)

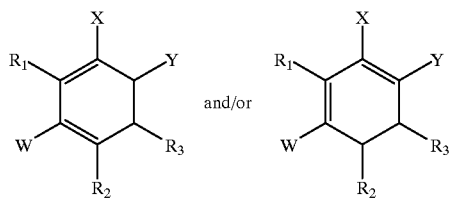

wherein X represents a phenyl group, a naphthyl group or a heteroaromatic group which are optionally substituted with $(C_1-C_4)$alkyl group(s), $(C_1-C_4)$alkoxy group(s), halogen atom(s) or nitro group(s); Y represents a $(C_1-C_4)$ alkoxycarbonyl group, a cyano group, a nitro group or a $(C_1-C_4)$alkoxysulfonyl group; W represents a halogen atom; $R_1$, $R_2$ and $R_3$ each independently represent a hydrogen atom, a $(C_1-C_4)$alkyl group, a $(C_1-C_4)$alkoxy group or a phenyl group which is optionally substituted with $(C_1-C_4)$ alkyl group(s), $(C_1-C_4)$alkoxy group(s) or halogen atom(s), followed by dehydro-, dehalogenation.

3. A process according to claim 2, wherein X represents a phenyl group or a pyridyl group which is optionally substituted with a methyl group or a nitro group; Y represents a methoxycarbonyl group, an ethoxycarbonyl group or a cyano group; W represents a chloride; $R_1$, $R_2$ and $R_3$ each represent a hydrogen atom.

4. A process according to claim 3, wherein said a cyclohexenone derivative represented by the formula (II):

(II)

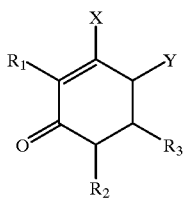

wherein X represents a phenyl group or a pyridyl group which is optionally substituted with a methyl group or a nitro group; Y represents a methoxycarbonyl group, an ethoxycarbonyl group or a cyano group; $R_1$, $R_2$ and $R_3$ each represent a hydrogen atom, is reacted with a chlorinating agent to obtain a chlorocyclohexadiene derivative or a mixture of isomers represented by the formula (IIIA and/or IIIB):

(IIIA and/or IIIB)

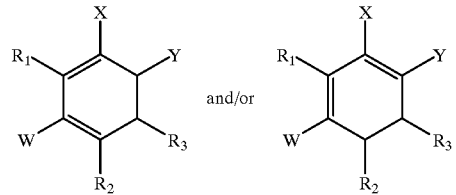

wherein X represents a phenyl group or a pyridyl group which is optionally substituted with a methyl group or a nitro group; Y represents a methoxycarbonyl group, an ethoxycarbonyl group or a cyano group; W represents a chloride; $R_1$, $R_2$ and $R_3$ each represent a hydrogen atom, followed by dehydro-, dechlorination by using alkaline metal alkoxides.

5. A process for preparing a benzene derivative represented by the formula (I):

(I)

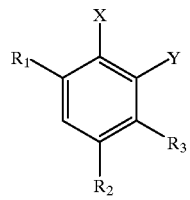

wherein X represents a phenyl group, a naphthyl group or a heteroaromatic group which are optionally substituted with $(C_1-C_4)$alkyl group(s), $(C_1-C_4)$alkoxy group(s), halogen atom(s) or nitro group(s); Y represents a $(C_1-C_4)$ alkoxycarbonyl group, a cyano group, a nitro group or a $(C_1-C_4)$alkoxysulfonyl group; $R_1$, $R_2$ and $R_3$ each independently represent a hydrogen atom, a $(C_1-C_4)$alkyl group, a $(C_1-C_4)$alkoxy group or a phenyl group which is optionally substituted with $(C_1-C_4)$alkyl group(s), $(C_1-C_4)$alkoxy group(s) or halogen atom(s); which comprises halogenating a cyclohexenone derivative represented by the formula (II):

(II)

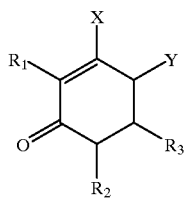

wherein X represents a phenyl group, a naphthyl group or a heteroaromatic group which are optionally substituted with $(C_1-C_4)$alkyl group(s), $(C_1-C_4)$alkoxy group(s), halogen atom(s) or nitro group(s); Y represents a $(C_1-C_4)$ alkoxycarbonyl group, a cyano group, a nitro group or a $(C_1-C_4)$alkoxysulfonyl group; $R_1$, $R_2$ and $R_3$ each independently represent a hydrogen atom, a $(C_1-C_4)$alkyl group, a $(C_1-C_4)$alkoxy group or a phenyl group which is optionally substituted with $(C_1-C_4)$alkyl group(s), $(C_1-C_4)$alkoxy group(s) or halogen atom(s), to obtain a halocyclohexadiene derivative or a mixture of isomers represented by the formula (IIIA and/or IIIB):

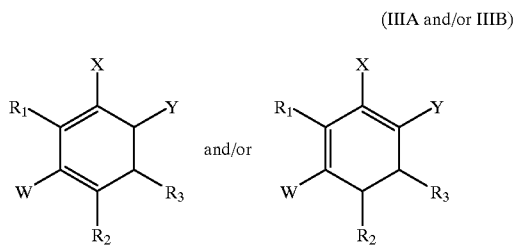
(IIIA and/or IIIB)

wherein X represents a phenyl group, a naphthyl group or a heteroaromatic group which are optionally substituted with $(C_1-C_4)$alkyl group(s), $(C_1-C_4)$alkoxy group(s), halogen atom(s) or nitro group(s); Y represents a $(C_1-C_4)$ alkoxycarbonyl group, a cyano group, a nitro group or a $(C_1-C_4)$alkoxysulfonyl group; W represents a halogen atom; $R_1$, $R_2$ and $R_3$ each independently represent a hydrogen atom, a $(C_1-C_4)$alkyl group, a $(C_1-C_4)$alkoxy group or a phenyl group which is optionally substituted with $(C_1-C_4)$ alkyl group(s), $(C_1-C_4)$alkoxy group(s) or halogen atom(s), followed by dehydrogenation to a halobenzene derivative represented by the formula (IV):

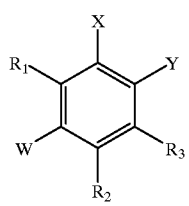
(IV)

wherein X represents a phenyl group, a naphthyl group or a heteroaromatic group which are optionally substituted with $(C_1-C_4)$alkyl group(s), $(C_1-C_4)$alkoxy group(s), halogen atom(s) or nitro group(s); Y represents a $(C_1-C_4)$ alkoxycarbonyl group, a cyano group, a nitro group or a $(C_1-C_4)$alkoxysulfonyl group; W represents a halogen atom; $R_1$, $R_2$ and $R_3$ each independently represent a hydrogen atom, a $(C_1-C_4)$alkyl group, a $(C_1-C_4)$alkoxy group or a phenyl group which is optionally substituted with $(C_1-C_4)$ alkyl group(s), $(C_1-C_4)$alkoxy group(s) or halogen atom(s), and reduction to a benzene derivative represented by the formula (I):

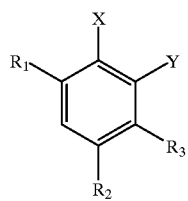

wherein X represents a phenyl group, a naphthyl group or a heteroaromatic group which are optionally substituted with $(C_1-C_4)$alkyl group(s), $(C_1-C_4)$alkoxy group(s), halogen atom(s) or nitro group(s); Y represents a $(C_1-C_4)$ alkoxycarbonyl group, a cyano group, a nitro group or a $(C_1-C_4)$alkoxysulfonyl group; $R_1$, $R_2$ and $R_3$ each independently represent a hydrogen atom, a $(C_1-C_4)$alkyl group, a $(C_1-C_4)$alkoxy group or a phenyl group which is optionally substituted with $(C_1-C_4)$alkyl group(s), $(C_1-C_4)$alkoxy group(s) or halogen atom(s).

6. A process according to claim 5, wherein X represents a phenyl group or pyridyl group which is optionally substituted with a methyl group or a nitro group; Y represents a methoxycarbonyl group, an ethoxycarbonyl group or a cyano group; W represents a chlorine atom; $R_1$, $R_2$ and $R_3$ each represent a hydrogen atom.

7. A process according to claim 6, wherein said a compound represented by the formula (II):

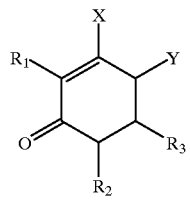

wherein X represents a phenyl group or pyridyl group which is optionally substituted with a methyl group or a nitro group; Y represents a methoxycarbonyl group, an ethoxycarbonyl group or a cyano group; $R_1$, $R_2$ and $R_3$ each represent a hydrogen atom, is reacted with a chlorinating agent to a chlorocyclohexadiene derivative or a mixture of isomers represented by the formula (IIIA and/or IIIB):

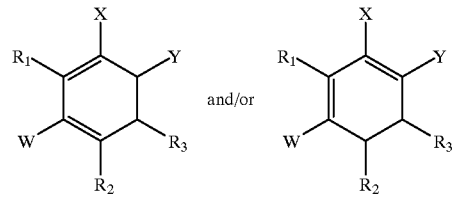
(IIIA and/or IIIB)

wherein X represents a phenyl group or pyridyl group which is optionally substituted with a methyl group or a nitro group; Y represents a methoxycarbonyl group, an ethoxycarbonyl group or a cyano group; W represents a chlorine atom; $R_1$, $R_2$ and $R_3$ each represent a hydrogen atom, followed by dehydrogenation to a chlorobenzene derivative represented by the formula (IV):

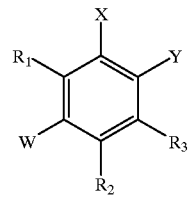
(IV)

wherein X represents a phenyl group or a pyridyl group which is optionally substituted with a methyl group or a nitro group; Y represents a methoxycarbonyl group, an ethoxycarbonyl group or a cyano group; W represents a chlorine atom; $R_1$, $R_2$ and $R_3$ each represent a hydrogen atom, and reduction to a benzene derivative represented by the formula (I):

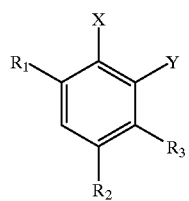

(I)

wherein X represents a phenyl group or a pyridyl group which is optionally substituted with a methyl group or a nitro group; Y represents a methoxycarbonyl group, an ethoxycarbonyl group or a cyano group; $R_1$, $R_2$ and $R_3$ each represent a hydrogen atom.

8. A process for preparing a benzene derivative represented by the formula (I):

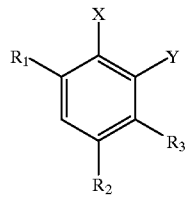

(I)

wherein X represents a phenyl group, a naphthyl group or a heteroaromatic group which are optionally substituted with $(C_1-C_4)$alkyl group(s), $(C_1-C_4)$alkoxy group(s), halogen atom(s) or nitro group(s); Y represents a $(C_1-C_4)$ alkoxycarbonyl group, a cyano group, a nitro group or a $(C_1-C_4)$alkoxysulfonyl group; $R_1$, $R_2$ and $R_3$ each independently represent a hydrogen atom, a $(C_1-C_4)$alkyl group, a $(C_1-C_4)$alkoxy c group or a phenyl group which is optionally substituted with $(C_1-C_4)$alkyl group(s), $(C_1-C_4)$alkoxy group(s) or halogen atom(s); which comprises reducing a cyclohexenone derivative represented by the formula (II):

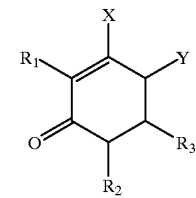

wherein X represents a phenyl group, a naphthyl group or a heteroaromatic group which are optionally substituted with $(C_1-C_4)$alkyl group(s), $(C_1-C_4)$alkoxy group(s), halogen atom(s) or nitro group(s); Y represents a $(C_1-C_4)$ alkoxycarbonyl group, a cyano group, a nitro group or a $(C_1-C_4)$alkoxysulfonyl group; $R_1$, $R_2$ and $R_3$ each independently represent a hydrogen atom, a $(C_1-C_4)$alkyl group, a $(C_1-C_4)$alkoxy group or a phenyl group which is optionally substituted with $(C_1-C_4)$alkyl group(s), $(C_1-C_4)$alkoxy group(s) or halogen atom(s), to obtain a cyclohexenol derivative represented by the formula (V):

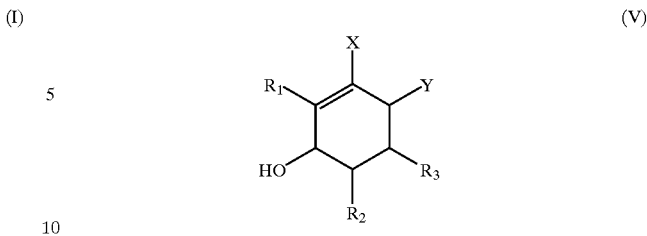

(V)

wherein X represents a phenyl group, a naphthyl group or a heteroaromatic group which are optionally substituted with $(C_1-C_4)$alkyl group(s), $(C_1-C_4)$alkoxy group(s), halogen atom(s) or nitro group(s); Y represents a $(C_1-C_4)$ alkoxycarbonyl group, a cyano group, a nitro group or a $(C_1-C_4)$alkoxysulfonyl group; $R_1$, $R_2$ and $R_3$ each independently represent a hydrogen atom, a $(C_1-C_4)$alkyl group, a $(C_1-C_4)$alkoxy group or a phenyl group which is optionally substituted with $(C_1-C_4)$alkyl group(s), $(C_1-C_4)$alkoxy group(s) or halogen atom(s), followed by dehydration to a cyclohexadiene derivative or a mixture of isomers represented by the formula (VIIA add/or VIIB):

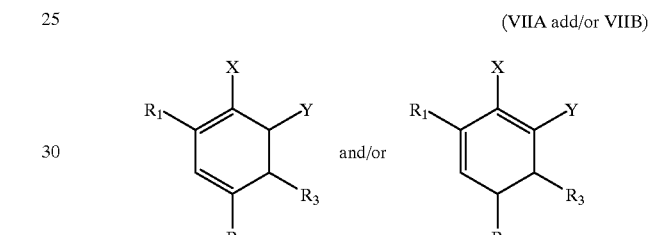

(VIIA add/or VIIB)

and/or wherein X represents a phenyl group, a naphthyl group or a heteroaromatic group which are optionally substituted with $(C_1-C_4)$alkyl group(s), $(C_1-C_4)$alkoxy group(s), halogen atom(s) or nitro group(s); Y represents a $(C_1-C_4)$ alkoxycarbonyl group, a cyano group, a nitro group or a $(C_1-C_4)$alkoxysulfonyl group; $R_1$, $R_2$ and $R_3$ each independently represent a hydrogen atom, a $(C_1-C_4)$alkyl group, a $(C_1-C_4)$alkoxy group or a phenyl group which is optionally substituted with $(C_1-C_4)$alkyl group(s), $(C_1-C_4)$alkoxy group(s) or halogen atom(s), and dehydrogenation to a benzene derivative represented by the formula (I):

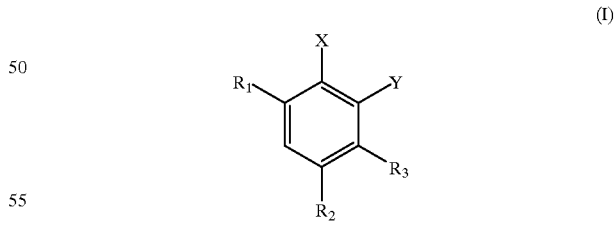

(I)

wherein X represents a phenyl group, a naphthyl group or a heteroaromatic group which are optionally substituted with $(C_1-C_4)$alkyl group(s), $(C_1-C_4)$alkoxy group(s), halogen atom(s) or nitro group(s); Y represents a $(C_1-C_4)$ alkoxycarbonyl group, a cyano group, a nitro group or a $(C_1-C_4)$alkoxysulfonyl group; $R_1$, $R_2$ and $R_3$ each independently represent a hydrogen atom, a $(C_1-C_4)$alkyl group, a $(C_1-C_4)$alkoxy group or a phenyl group which is optionally substituted with $(C_1-C_4)$alkyl group(s), $(C_1-C_4)$alkoxy group(s) or halogen atom(s).

9. A process according to claim 8, wherein X represents a phenyl group or a pyridyl group which is optionally substituted with a methyl group or a nitro group; Y represents a methoxycarbonyl group, an ethoxycarbonyl group or a cyano group; $R_1$, $R_2$ and $R_3$ each represent a hydrogen atom.

10. A process according to claim 9, wherein said a benzene derivative represented by the formula (I):

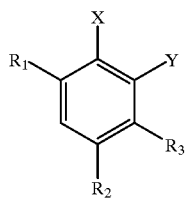
(I)

wherein X represents a phenyl group or a pyridyl group which is optionally substituted with a methyl group or a nitro group; Y represents a methoxycarbonyl group, an ethoxycarbonyl group or a cyano group; $R_1$, $R_2$ and $R_3$ each represent a hydrogen atom, is reduced by sodium borohydride to obtain a cyclohexnenol derivative represented by the formula (V):

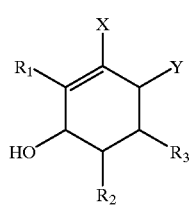
(V)

wherein X represents a phenyl group or a pyridyl group which is optionally substituted with a methyl group or a nitro group; Y represents a methoxycarbonyl group, an ethoxycarbonyl group or a cyano group; $R_1$, $R_2$ and $R_3$ each represent a hydrogen atom, followed by dehydration to a cyclohexadiene derivative or a mixture of isomers represented by the formula (VIIA add/or VIIB):

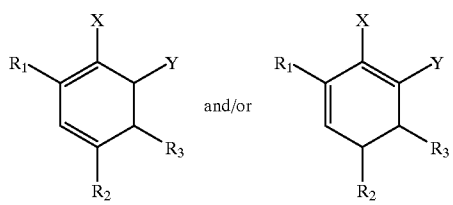
(VIIA and/or VIIB)

wherein X represents a phenyl group or a pyridyl group which is optionally substituted with a methyl group or a nitro group; Y represents a methoxycarbonyl group, an ethoxycarbonyl group or a cyano group; $R_1$, $R_2$ and $R_3$ each represent a hydrogen atom, and dehydrogenation to a benzene derivative represented by the formula (I):

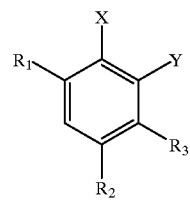
(I)

wherein X represents a phenyl group or a pyridyl group which is optionally substituted with a methyl group or a nitro group; Y represents a methoxycarbonyl group, an ethoxycarbonyl group or a cyano group; $R_1$, $R_2$ and $R_3$ each represent a hydrogen atom.

11. A process according to claim 9, wherein said benzene derivative represented by the formula (I):

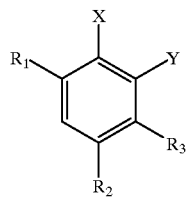

wherein X represents a phenyl group or a pyridyl group which is optionally substituted with a methyl group or a nitro group; Y represents a methoxycarbonyl group, an ethoxycarbonyl group or a cyano group; $R_1$, $R_2$ and $R_3$ each represent a hydrogen atom, is reduced by sodium borohydride to obtain a cyclohexenol derivative represented by the formula (V)

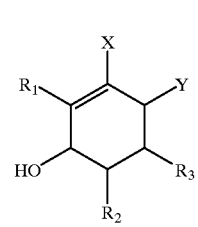
(V)

wherein X represents a phenyl group or a pyridyl group which is optionally substituted with a methyl group or a nitro group; Y represents a methoxycarbonyl group, an ethoxycarbonyl group or a cyano group; $R_1$, $R_2$ and $R_3$ each represent a hydrogen atom, followed by conversion to a cyclohexene derivative represented by the formula (VI):

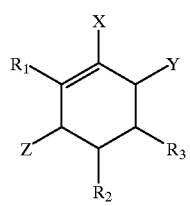

wherein X represents a phenyl group or a pyridyl group which is optionally substituted with a methyl group or a nitro group; Y represents a methoxycarbonyl group, an ethoxycarbonyl group or a cyano group; Z represents a halogen atom $R_1$, $R_2$ and $R_3$ each represent a hydrogen atom, and a $(C_1-C_6)$acyloxy group, a $(C_1-C_6)$ alkoxycarbonyloxy group, a N,N-di$(C_1-C_4)$alkylcarbamoyloxy group, a $(C_1-C_4)$alkylsulfonyloxy group, a benzenesulfonyl group which is optionally substituted with a $(C_1-C_4)$alkyl group, a $(C_1-C_4)$alkoxy group, a halogen atom, and elimination to a cyclohexadiene derivative or a mixture of isomers represented by the formula (VIIA and/or VIIB):

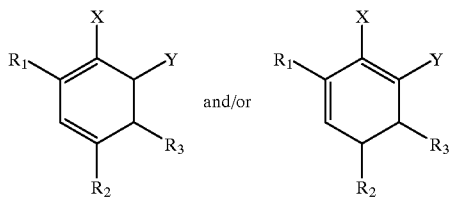

wherein X represents a phenyl group or a pyridyl group which is optionally substituted with a methyl group or a nitro group; Y represents a methoxycarbonyl group, an ethoxycarbonyl group or a cyano group; $R_1$, $R_2$ and $R_3$ each represent a hydrogen atom, and dehydrogenation to a benzene derivative represented by the formula (I):

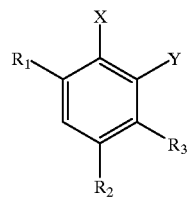

(I)

wherein X represents a phenyl group or a pyridyl group which is optionally substituted with a methyl group or a nitro group; Y represents a methoxycarbonyl group, an ethoxycarbonyl group or a cyano group $R_1$, $R_2$ and $R_3$ each represent a hydrogen atom.

12. A process according to claim 11, wherein Z represents a chlorine atom.

* * * * *